United States Patent
Paitel et al.

(10) Patent No.: US 10,070,802 B2
(45) Date of Patent: *Sep. 11, 2018

(54) METHODS AND APPARATUS FOR ELECTROMAGNETIC NAVIGATION OF A MAGNETIC STIMULATION PROBE

(71) Applicant: Medtronic Navigation, Inc., Louisville, CO (US)

(72) Inventors: Yvan Paitel, Louisville, CO (US); Steven L. Hartmann, Superior, CO (US); Lilac Muller, Nederland, CO (US)

(73) Assignee: Medtronic Navigation, Inc., Louisville, CO (US)

(*) Notice: Subject to any disclaimer, the term of this patent is extended or adjusted under 35 U.S.C. 154(b) by 895 days.

This patent is subject to a terminal disclaimer.

(21) Appl. No.: 14/034,190

(22) Filed: Sep. 23, 2013

(65) Prior Publication Data

US 2014/0024920 A1    Jan. 23, 2014

Related U.S. Application Data

(63) Continuation of application No. 12/104,550, filed on Apr. 17, 2008, now Pat. No. 8,543,189.

(Continued)

(51) Int. Cl.
*A61B 5/06* (2006.01)
*A61B 6/03* (2006.01)
(Continued)

(52) U.S. Cl.
CPC .............. *A61B 5/06* (2013.01); *A61B 5/055* (2013.01); *A61B 5/743* (2013.01); *A61B 6/032* (2013.01);
(Continued)

(58) Field of Classification Search
CPC ....................................................... A61B 5/05
(Continued)

(56) References Cited

U.S. PATENT DOCUMENTS 5,318,561 A * 6/1994 McLeod ................. A61N 2/02
600/14
5,483,158 A * 1/1996 van Heteren ...... G01R 33/3628
324/318

(Continued)

FOREIGN PATENT DOCUMENTS

EP          1510182         3/2005
EP          1563870         8/2005
WO      WO-2004035135       4/2004

OTHER PUBLICATIONS

DiCarlo et al. Electromagnetic field-induced protection of chick embryos against hypoxia exhibits characteristics of temporal sensing. 2000 Bioelectrochem. 52:17-21.*

(Continued)

*Primary Examiner* — Tse Chen
*Assistant Examiner* — Patrick M Mehl
(74) *Attorney, Agent, or Firm* — Harness Dickey

(57) ABSTRACT

A system and method is disclosed that can be used to track and navigate an instrument relative to a patient. The system can include an electromagnetic tracking system to track an electromagnetic stimulation probe, such as a transcranial magnetic stimulation probe. The system can, according to various embodiments, provide a tracking device on the probe, track the coil of the probe, provide a field relative to the probe, and determine the position of the patient based upon the field produced by the probe.

20 Claims, 5 Drawing Sheets

Related U.S. Application Data

(60) Provisional application No. 60/913,459, filed on Apr. 23, 2007.

(51) Int. Cl.
*A61B 5/055* (2006.01)
*A61N 2/00* (2006.01)
*A61B 5/00* (2006.01)
*A61B 90/00* (2016.01)
*A61B 34/20* (2016.01)
*A61B 34/10* (2016.01)

(52) U.S. Cl.
CPC .............. *A61B 6/037* (2013.01); *A61B 34/20* (2016.02); *A61B 90/36* (2016.02); *A61N 2/00* (2013.01); *A61B 2034/107* (2016.02); *A61B 2034/2051* (2016.02); *A61B 2090/376* (2016.02); *A61B 2090/397* (2016.02)

(58) Field of Classification Search
USPC .......................... 600/407, 409, 424; 128/920
See application file for complete search history.

(56) References Cited

U.S. PATENT DOCUMENTS

| | | | |
|---|---|---|---|
| 5,592,939 | A | 1/1997 | Martinelli |
| 5,740,808 | A | 4/1998 | Panescu et al. |
| 5,913,820 | A * | 6/1999 | Bladen ............... A61B 5/06 128/899 |
| 6,246,896 | B1 | 6/2001 | Dumoulin et al. |
| 6,381,485 | B1 | 4/2002 | Hunter et al. |
| 6,474,341 | B1 | 11/2002 | Hunter et al. |
| 6,527,695 | B1 | 3/2003 | Davey et al. |
| 6,827,681 | B2 | 12/2004 | Tanner et al. |
| 6,830,544 | B2 | 12/2004 | Tanner et al. |
| 7,008,370 | B2 | 3/2006 | Tanner et al. |
| 7,087,008 | B2 | 8/2006 | Fox et al. |
| 7,697,972 | B2 | 4/2010 | Verard et al. |
| 2003/0004392 | A1 | 1/2003 | Tanner et al. |
| 2004/0138550 | A1* | 7/2004 | Hartlep ............... A61N 2/02 600/407 |
| 2004/0171924 | A1* | 9/2004 | Mire ................ A61B 19/5244 600/407 |
| 2004/0199072 | A1* | 10/2004 | Sprouse ............... A61B 5/06 600/424 |
| 2004/0215071 | A1 | 10/2004 | Frank et al. |
| 2005/0085720 | A1 | 4/2005 | Jascob et al. |
| 2007/0066887 | A1 | 3/2007 | Mire et al. |
| 2008/0262338 | A1 | 10/2008 | Paitel et al. |

OTHER PUBLICATIONS

Ruohonen. Transcranial Magnetic Stimulation Modelling and new techniques. 1998 Ph.D. Thesis, Helsinki University of Technology 52 pages.*
Rushworth et al. Complementary localisation and lateralisation of orienting and motor attention. 2001 Nature Neuroscience 4:656-661.*
Sommer et al. Transcranial magnetic stimulation—a sandwich coil design for a better sham. 2006 Clin.Neurophysiol. 117:440-446.*
"Applications:", Medtronic, Inc., 2006, http://www.medtronic.com/intl/neurophysiology/magproapplications.html printed Feb. 21, 2007.
"Butterfly Coil", Product Information Sheet, MCF-B65 for MagPro, Medtronic A/S, Publ. No. 8064E, Oct. 2004.
"Figure-of-8 Coils—magnetic and electric fields", Medtronic A/S, Jun. 9, 2005.
"MagPro X100 User Guide", Medtronic A/S, Copyright 2003.
"MagPro", Medtronic, Inc., 2006, http://www.medtronic.com/intl/neurophysiology/magpro.html printed Feb. 21, 2007.
Bohning, D.E., et al., "Mapping Transcranial Magnetic Stimulation (TMS) fields in vivo with MRI", Neuroreport, Lippincott Williams & Wilkins, US, vol. 8, No. 11, Jul. 28, 1997 (Jul. 28, 1997), pp. 2535-2538, XP002116991, ISSN: 0959-4965, p. 2535-p. 2538.
Ettinger, G.J., et al., "Non-Invasive Functional Brain Mapping Using Registered Transcranial Magnetic Stimulation", Digital Library, 1996 Workshop on Mathematical Methods in Biomedical Image Analysis (MMBIA '96) p. 0032, <http://csdl2.computer.org/persagen/DLAbsToc.jsp?resourcePath=/dl/proceedings/&toc=com> . . . ; abstract printed Jan. 1, 2007 (2 pages).
Ettinger, G.J., et al., Non-Invasive Functional Brain Mapping Using Registered Transcranial Magnetic Stimulation, http://splweb.bwh.harvard.edu:8000/pages/papers/ettinger/tms.paper/text.html printed Jan. 1, 2007 (14 pages.).
International Search Report and Written Opinion for PCT/US2008/004957 dated Oct. 14, 2008 claiming benefit of U.S. Appl. No. 60/913,459, filed Apr. 23, 2007.
Oliver, J., et al., "Frameless Stereotactically Guided Transcranial Magnetic Stimulation: A Refined Protocol", Motor Control and Cognitive Neuroscience Conference, Dunedin, NZ, Dec. 6-9, 2005.
Reid, C., et al., "Integrating Stereotactic Transcranial Magnetic Stimulation (TMS) and EEG: Artefact Removal, Co-registration and Source Localisation Issues", Motor Control and Cognitive Neuroscience Conference, Dunedin, NZ, Dec. 6-9, 2005.

* cited by examiner

METHODS AND APPARATUS FOR ELECTROMAGNETIC NAVIGATION OF A MAGNETIC STIMULATION PROBE

CROSS-REFERENCE TO RELATED APPLICATIONS

This application is a continuation of U.S. application Ser. No. 12/104,550 filed on Apr. 17, 2008, which claims the benefit of U.S. Provisional Application No. 60/913,459, filed on Apr. 23, 2007. The disclosures of the above applications are incorporated herein by reference.

FIELD

The present disclosure is directed to a surgical navigation system, and particularly to a navigation system and planning system to navigate a stimulation probe to direct stimulation to a selected or planned region of an anatomy.

BACKGROUND

The statements in this section merely provide background information related to the present disclosure and may not constitute prior art.

Surgical procedures can be performed on a patient for various purposes. Surgical procedures can use multiple techniques and instruments. Because many procedures are performed within or affect a patient's internal anatomy, it is desirable to provide a system that allows a determination of a position of an instrument, an implant, or a treatment affect relative to the patient during an operative procedure.

Imaging devices can provide image data of portions of the patient, both internal and external. For example, a fluoroscope, magnetic resonance imager, etc. can be provided to obtain image data of a selected portion of the patient's anatomy. The image data can be used to view a selected portion of the anatomy. It is desirable, however, to provide the image data to plan or select an appropriate or optimum therapy factor. Therefore, it is desirable to provide a system that allows for ease and efficiency of determining a position of an instrument relative to the patient for viewing on a display. This can assist in determining a position of the instrument or implant relative to the patient during an operative procedure. It is also desirable to provide a system that assists in determining a position and instrument that provides an optimized therapy to an affected region.

A tracking or navigation system can be used to track and determine the position of a probe or device relative to the anatomy. It is desired, however, to provide a navigation system and tracking system that is operable to determine the position to a probe relative to a portion of the anatomy for a probe in a non-invasive configuration. It is further desirable to provide a system that is operable to determine the position of a probe to further determine the location of a therapy or stimulation being provided to the anatomy by the probe. It is desirable to provide such a tracking system to determine the position of the device and to plan the appropriate positioning of a device for providing a therapy or stimulation to the anatomy.

The tracking or navigation of a non-invasive probe can be performed with an optical system. An optical system, however, requires line or sight, a tracking device affixed to the probe. etc. The tracking device can be large or cumbersome, in various designs. In addition, the optical tracking device requires an additional component added to the probe. It is desirable, therefore, to provide a small tracking device or eliminate the need for a separate tracking device on the probe.

SUMMARY

Further areas of applicability will become apparent from the description provided herein. It should be understood that the description and specific examples are intended for purposes of illustration only and are not intended to limit the scope of the present disclosure.

A system and method are disclosed for tracking and navigating a non-invasive instrument relative to the anatomy. The non-invasive instrument probe can include a transcranial magnetic stimulator (TMS) probe. The TMS probe can include one or more coils operable to produce an electric field near or at a position relative to the coil. The coil can be energized in any appropriate manner to provide the magnetic field. The TMS probe is exemplary of any appropriate instrument which can include a magnetic stimulation device.

Further, the TMS probe can be navigated according to various embodiments. For example, the probe can be navigated by positioning a tracking device on the TMS probe. The tracking device, according to various embodiments, can include a wire coil, as discussed further herein. A localizing or tracking system can further include a coil system operable to transmit an electromagnetic field to allow tracking of the tracking device positioned on the TMS probe.

According to various embodiments, the coils of the TMS probe can be used as the tracking device, this can eliminate the need for a separate tracking device. The localizer system can emit a field which can be used to track the TMS probe. According to various embodiments, the patient or other portion relative to which the TMS probe is being navigated can include a tracking device. The tracking device positioned on the patient can be referred to as a dynamic reference frame. The localizer system can be integrated with or attached to the TMS probe. Therefore, the localizer or system can produce a field that the dynamic reference frame can sense and determine a position relative to the localizer array which is affixed or integrated with the TMS probe. According to various embodiments, the TMS probe, as discussed above including a coil operable to produce an electromagnetic field, can act as a localizer system. The patient can further include a dynamic reference frame to sense the field produced by the TMS probe. It will be understood, as further discussed herein, that the localizer system can transmit a field, receive a field, or combinations thereof. Therefore, the tracking device, either provided with the TMS probe or with the dynamic reference frame, can also emit a field, receive a field, or combinations thereof. Therefore, it will be understood that the discussion of a portion transmitting a field and another portion receiving the field is merely exemplary and the system can also operate in reverse.

According to various embodiments, a system to navigate a non-invasive procedure for a patient is disclosed. The system can include an electromagnetic tracking system including an electromagnetic localizer system. The system can also include a magnetic stimulation probe operable to produce a probe electromagnetic field, wherein the probe electromagnetic field is operable to induce a current in a conductive material. A processor system can determine the position of a magnetic stimulation probe relative to the patient based at least in part on the field produced by the electromagnetic localizer system. The magnetic stimulation probe is operable to stimulate a selected portion of the patient.

According to various embodiments, system to navigate a non-invasive procedure on an anatomy is disclosed. The system can include an instrument having at least one coil of conductive material and a controller operable to drive a current through the coil so that the coil produces an electromagnetic field. An imaging device can obtain image data of the anatomy. An electromagnetic tracking system can detect a position of the instrument relative to the anatomy. A display device is operable to display the image data of the anatomy and an icon representing the instrument. In addition, a processor system can determine the position of the instrument relative to the anatomy and draw the icon with the display device of the instrument at a location representing the position of the instrument relative to the anatomy.

According to various embodiments, a method of navigating a magnetic stimulation probe relative to an anatomy is disclosed. The method can be used to determine a focal region of an electromagnetic field produced by the magnetic stimulation probe. The magnetic stimulation probe can be tracked with an electromagnetic tracking system. Image data of the anatomy can be obtained and displayed on a display device. In addition, an icon representing a position of the focal region superimposed on the displayed image data based upon the tracked location of the magnetic stimulation probe.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
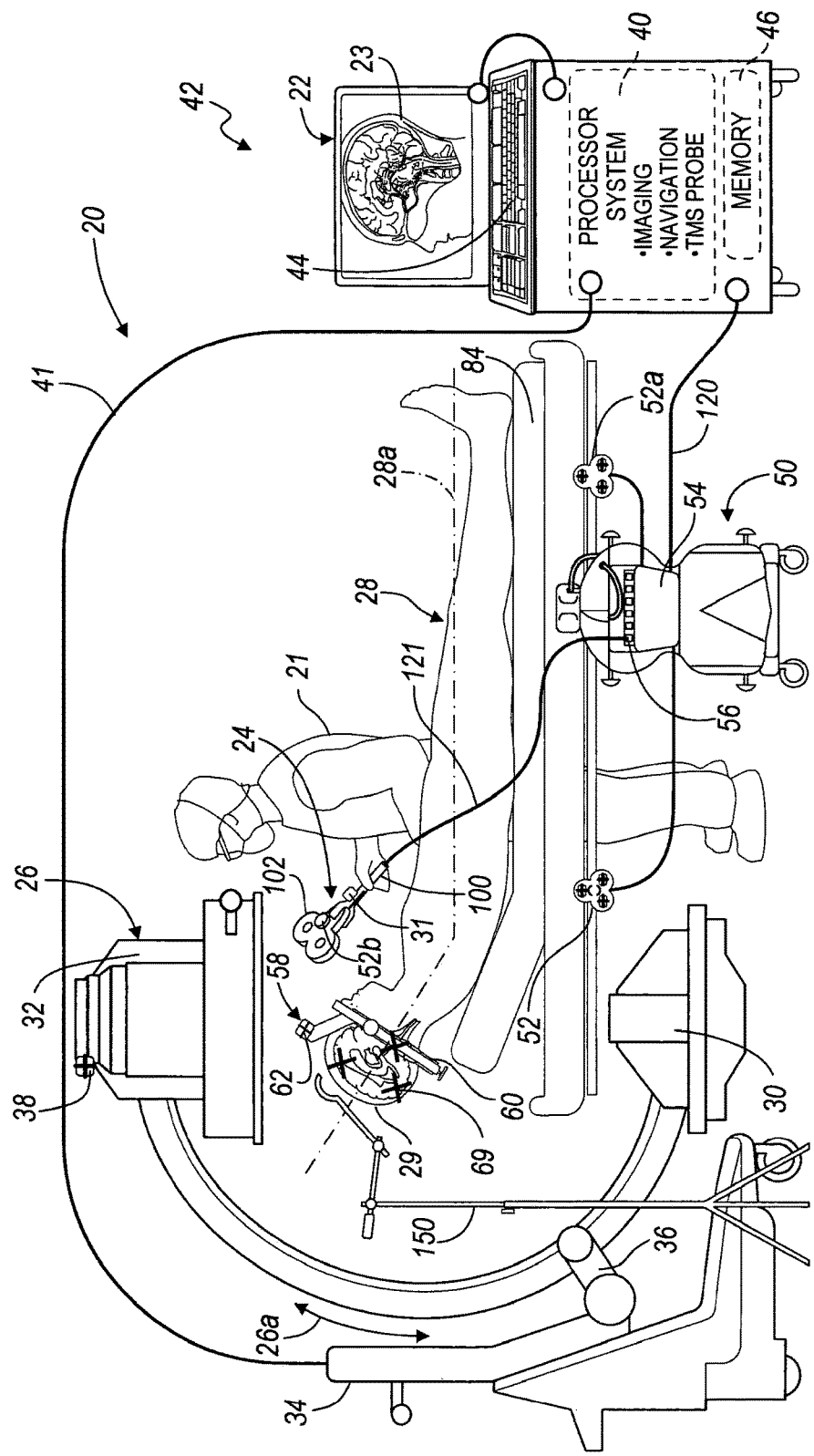
FIG. 1 is an environmental view of a surgical navigation system according to various embodiments.

A guided or navigated procedure can be performed with a navigation system 20, illustrated in FIG. 1. The guided procedure can be any appropriate procedure, such as a neural procedure, spinal procedure, or an orthopedic procedure. The navigation system 20 can include various components, as will be discussed further herein. The navigation system 20 can allow a user, such as a surgeon 21 to view on a display device 22 a relative position of an instrument 24 to a coordinate system. The coordinate system can be relative to image data displayed on the display device 22, to a patient only, to a point outside of a patient, or combinations of these. Further, the navigation system 20 can be used with image data, imageless or without image data, atlas data specific image data, or combinations of these.

It should further be noted that the navigation system 20 can be used to navigate or track various instruments including: cannulas, catheters, probes, needles, guidewires, instruments, implants, deep brain stimulators, electrical leads, magnetic stimulators, etc. Moreover, the instrument 24 can be used in any region of the body. The navigation system 20 and the instrument 24 can be used in any appropriate procedure, such as one that is generally minimally invasive, arthroscopic, percutaneous, stereotactic, or an open procedure.

Also, the single illustrated instrument 24 is only exemplary of any appropriate instrument and may also represent many instruments, such as a series or group of instruments. Identity and other information relating to the instrument 24 can also be provided to the navigation system 20. Information from an instrument tracking device 31 can be transmitted along an information system 25 to the workstation. Further, the information about the instrument 24 can also be displayed on the display device 22 for viewing by the surgeon 21.

The navigation system 20 can include an imaging device 26 that is used to acquire pre-, intra-, or post-operative or real-time image data of a patient 28. The imaging device 26 can be, for example, a fluoroscopic x-ray imaging device that may be configured as, and also referred to as, a C-arm 26 having an x-ray source 30 and an x-ray receiving section 32. The sections can be mounted relative to one another and moveable relative to a base 35. The base 35 can be fixed relative to the patient 28. An optional calibration and tracking target and optional radiation sensors can be provided, as understood by one skilled in the art. An example of a fluoroscopic C-arm x-ray device that may be used as the imaging device 26 is the ARCADIS® Orbic or ARCADIS® Orbic 3D from Siemens Medical of Germany. Other exemplary fluoroscopes include bi-plane fluoroscopic systems, ceiling fluoroscopic systems, cath-lab fluoroscopic systems, fixed C-arm fluoroscopic systems, 3D fluoroscopic systems, O-arm™ imaging devices (i.e. devices sold by Breakaway Imaging, LLC. having a place of business in Massachusetts, USA), etc.

An optional imaging device controller 34 can control the imaging device 26 to capture the x-ray images received at the receiving section 32 and store the images for later use. The receiving section 32 can also be referred to as or act as, according to various embodiments, an image collection section or image intensifier. The controller 34 may also be separate from the C-arm 26 or located a distance from the C-arm 26. The controller 34 can control the C-arm 26 to control movement in the direction of arrow 26*a* or rotate about a longitudinal axis 28*a* of the patient 28, allowing anterior or lateral views of the patient 28 to be imaged. Each of these movements involves rotation about a mechanical axis 36 of the C-arm 26.

The operation of the C-arm 26 is understood by one skilled in the art and not repeated in detail here. Briefly, however, x-rays can be emitted from an x-ray section 30 and received at a receiving section 32. The receiving section 32 can include a camera that can create the image data from the received x-rays. Further, a C-arm tracking device 38 can be provided to track a position of any portion of the C-arm 26, such as the receiving section 32, at any appropriate time by the tracking system 50.

It will be understood that image data can be created or captured with any appropriate imaging device, such as a magnetic resonance imaging system, a positron emission tomography system, computed tomography, or any appropriate system. It will be further understood that various imaging systems can be calibrated according to various known techniques. The use of the C-arm 26, however, can be used according to various embodiments disclosed herein.

The image data can be forwarded from the C-arm controller 34 to a navigation computer and/or processor system 40 via a communication system 41. The communication system 41 can be wireless, wired, a data transfer device (e.g. a CD-Rom or DVD-Rom), or any appropriate system. The processor system 40 can also include the C-arm controller 34. The C-arm controller 34 and the processor system 40 can also, therefore, include a BUS communication system or internal communication. It will also be understood that the image data is not necessarily first retained in the controller 34, but may be directly transmitted to a workstation 42 or to a tracking system 50, as discussed herein.

A work station 42 can include the processor system 40, the display device 22, a user interface 44, and a memory 46. The processor system 40 can process the image data, navigation data, planning data, treatment area data, etc. The processor system 40 can include one or multiple separate processors to execute selected instructions or perform various tasks.

The work station 42 provides facilities for displaying the image data 23 as an image on the display device 22, saving, digitally manipulating, or printing a hard copy image of the received image data 23. The user interface 44 may be a keyboard, mouse, touch pen, touch screen or other suitable device. The user interface device 44 allows a physician or user to provide inputs to control the imaging device 26, via the C-arm controller 34, or adjust the display settings of the display device 22. The user interface 44 can also allow a user to manipulate the navigation system 20 in any selected manner.

While the imaging device 26 is shown in FIG. 1, any other alternative 2D, 3D or 4D imaging modality may also be used. As disclosed herein any appropriate imaging system can be used in the navigation system to provide image data. The imaging system 26 can generally provide information regarding movement of a capturing or receiving section 32 thereof to determine a position of the capturing portion relative to the patient 28. For example, any 2D, 3D or 4D imaging device, such as isocentric fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative CT, single photo emission computed tomography (SPECT), or planar gamma scintigraphy (PGS) may also be used to acquire 2D, 3D or 4D pre- or post-operative and/or real-time images or image data of the patient 28. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion of optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, can also provide functional image data superimposed onto anatomical data to be used to confidently reach target sites within the patient 28. It should further be noted that the optional imaging device 26, as shown in FIG. 1, provides a virtual bi-plane image using a single-head C-arm fluoroscope as the optional imaging device 26 by simply rotating the C-arm 26 about at least two planes, which could be orthogonal planes to generate two-dimensional images that can be converted to three-dimensional volumetric images. By acquiring images in more than one plane, an icon representing the location of an impacter, stylet, reamer driver, taps, drill, deep brain stimulators, electrical leads, needles, implants, probes, or other instrument, introduced and advanced in the patient 28, may be superimposed in more than one view on the display device 22. Displaying an icon in multiple views can allow simulated bi-plane or even multi-plane views, including two and three-dimensional views.

With continuing reference to FIG. 1, the navigation system 20 can further include a tracking system, such as an electromagnetic (EM) tracking system 50 that includes a localizer 52 (e.g. a coil array or multiple coil arrays), a coil array controller 54, a navigation interface 56 for an instrument tracking device, and a dynamic reference frame 58. The dynamic reference frame 58 can be used to determine at any point in time, a position of the patient 28 in the navigated space. One skilled in the art will understand, however, that any appropriate navigation system can be used, such as an optical navigation system, a radar navigation system, an acoustic navigation system, an accelerometer navigation system, etc.

The dynamic reference frame 58 can include a dynamic reference frame member or holder 60 and a removable tracking device 62. Alternatively, the dynamic reference frame 58 can include a tracking device that is formed integrally with the dynamic reference frame member 60. One skilled in the art will understand that the tracking device 62 can be any appropriate device that can be an emitter, a receiver, a reflector, a sensor to sense a field, or any other appropriate device that can be tracked by a tracking system including the localizer 52.

The localizer coil array 52 may also be supplemented or replaced with a second localizer 52a. The second localizer 52a may be the same as the first localizer 52 or different, such as that described in U.S. patent application Ser. No. 10/941,782, filed Sep. 15, 2004, now U.S. Pat. App. Pub. No. 2005/0085720, and entitled "METHOD AND APPARATUS FOR SURGICAL NAVIGATION", herein incorporated by reference.

As is understood, the localizer array 52 can transmit signals that are received by an appropriate tracking device. The signal transmitted by the localizer 52 can be an electromagnetic field that will have a different strength at any position in the field. The coil array 52 can include a plurality of coils each operable to generate distinct electromagnetic fields into the navigation region of the patient 28, which is sometimes referred to as patient space. Electromagnetic systems are generally described in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The tracking device, such as the tracking device 62 of the dynamic reference frame 58, an instrument tracking device 31 on the instrument 24, the tracking device 38 on the imaging device 26, etc. can sense the field strength at their respective locations. The tracking device 62 of the dynamic reference frame 58, the instrument tracking device 31, and the tracking device 38 can then transmit signals based upon the received signals from the array 52, 52a. One skilled in the art will also understand that the localizer 52, 52a can receive or sense a field produced by the various tracking devices 62, 31, and 38. Thus the system can work in either manner or a combination.

It should further be noted that the entire tracking system 50 or parts of the tracking system 50 may be incorporated into the imaging device 26. For example, one of the localizers can be incorporated into the imaging device 26. Incorporating the tracking system 50 may provide an integrated imaging and tracking system. Any combination of these components may also be incorporated into the imaging system 26, which can include any appropriate imaging device.

The coil array 52, which can include multiple individual coils, can be positioned at any appropriate location. For example it can be attached to the receiving section 32 of the C-arm 26. Alternatively, the coil array 52 may be positioned at the x-ray source 30, within or atop an operating room (OR) table 84, on siderails associated with the OR table 84, or positioned on the patient 28. The coil array 52 may also be positioned in the items being navigated.

The coil array 52 is controlled or driven by the coil array controller 54. The coil array controller 54 can drive each coil in the coil array 52 in a time division multiplex or a frequency division multiplex manner. In this regard, each coil may be driven separately at a distinct time or all of the coils may be driven simultaneously with each being driven at a different frequency, as discussed further herein. This arrangement makes the coil array 52 a transmitter coil array. It will be understood that the coil array may also receive or sense a field, as discussed above. Thus, reference to a transmitter coil array is merely exemplary and not intended to limit the type of localizer used in a selected tracking system.

Upon driving the coils in the transmitter coil array 52 with the coil array controller 54, electromagnetic fields are generated within the patient 28, which is sometimes referred to as patient space. The electromagnetic fields generated in the patient space induce currents to produce signals in the tracking devices 31, 38, 62 positioned in the navigation field. These induced signals are delivered to the navigation device interface 56 and can be forwarded to the coil array controller 54, as discussed above. Again, it will be understood that the tracking devices may transmit a field and induce a signal in the localizer 52.

The navigation device interface 54 may provide all the necessary electrical isolation for the navigation system 20, as discussed herein. The navigation device interface 56 can also include amplifiers, filters and buffers to directly interface with the tracking devices 31, 38, 62. Alternatively, the tracking devices 31, 38, 62 or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled with a physical transmission line to the navigation device interface 56.

When the navigation system 20 uses an EM based tracking system, various portions of the navigation system 20 are equipped with at least one coil and generally multiple coils. The coils can be used with the EM localizer arrays 52, 52a to determine a position of the coils. The coils are generally defined by tracking devices 31, 38, 62 that are associated with the portions to be tracked. Thus, determining a position of the coils allows a determination of a position of the tracking devices and the portions to which they are attached. Alternatively, the tracking system 50 may be a hybrid system that includes components from various tracking systems such as optical, acoustic, radiation, radar, etc.

The tracking device 31 on the instrument 24 can be in a handle or inserter that interconnects with an attachment portion. The instrument 24 can include a graspable or manipulable portion at a proximal end at the tracking device and can be fixed near the manipulable portion of the instrument 24 or at a distal working end. The tracking device 24 can include an electromagnetic sensor to sense the electromagnetic field generated by the transmitter coil array 52 that can induce a current in the tracking device 31, or vice versa as discussed above.

Figure 2:
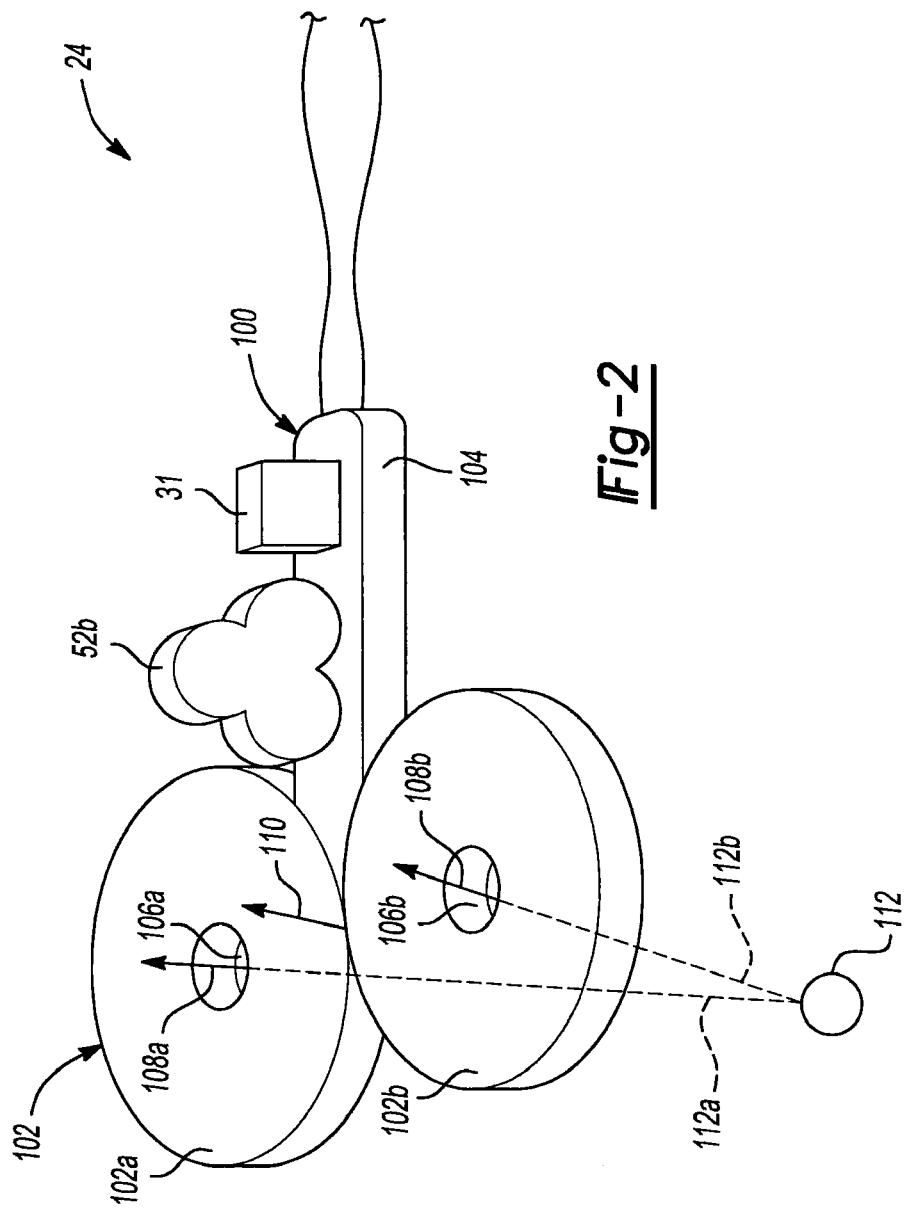
FIG. 2 is a detail view of a magnetic stimulation device.

The instrument 24 can include a magnetic stimulation probe, such as a transcranial magnetic stimulation (TMS) probe 100, illustrated in detail in FIG. 2. The TMS probe 100 can include the tracking device 31 positioned at an appropriate location. The tracking device 31 can, for example, be positioned anywhere on the TMS probe 100 if the TMS probe 100 is substantially rigid. The tracking device 31 can also be positioned substantially near a distal or working end 102 of the TMS probe 100. Also, an additional or alternative localizing system 52b can be provided associated with the TMS probe 100.

The tracking device 31, either alone or in combination with a guide device, can be used by the tracking system 50 to determine the location of the working end or coil portion 102 of the TMS probe 100. Therefore, the position of the TMS probe 100 can be determined based upon the tracked position of the tracking device 31. The coil portion 102, as discussed further herein, can include stimulation coils. The stimulation coils can produce a field that is focused at a selected position in space. The tracking device 31, in addition to the navigation system 20 including the tracking system 50, can be used to determine the position of the focal point in space relative to any appropriate portion of the patient space.

Each of the tracking devices 31, 38, 62 can also be coupled to the navigation device interface 56 to forward the information to the coil array controller 54. For example, the dynamic reference frame 58, according to various embodiments, may include a small magnetic field detector as the tracking device 62. The dynamic reference frame 58 may be fixed to the patient 28 adjacent to the region being navigated so that any movement of the patient 28 is detected as relative motion between the transmitter coil array 52 and the dynamic reference frame 58. The dynamic reference frame 58 can be interconnected with the patient 28 in any appropriate manner, including those discussed herein. Any relative motion is forwarded to the coil array controller 54, which updates registration correlation and maintains accurate navigation, further discussed herein. An electromagnetic dynamic reference frame 58 can be configured as a pair or trio of orthogonally oriented coils, each having the same center or may be configured in any other non-coaxial or co-axial coil configurations.

The dynamic reference frame 58 may be affixed externally to the patient 28, adjacent to the region of navigation, such as on the patient's cranium, etc., as shown in FIG. 1. The dynamic reference frame 58 can be affixed to the patient's skin, by way of a selected adhesive patch and/or a tensioning system. The dynamic reference frame 58 may also be removably attachable to a fiducial marker 69. The fiducial markers can be anatomical landmarks or members attached or positioned on the patient's 28 body. The dynamic reference frame 58 can also be connected to a bone portion of the anatomy. The bone portion can be adjacent the area of the procedure, the bone of the procedure, or any appropriate body portion.

Although the discussion above is directed to an electromagnetic navigation and tracking system, it will be understood that any appropriate tracking system can be used as the tracking system 50. For example, one skilled in the art will understand that appropriate tracking systems include, but are not limited to, an optical tracking system, a radar tracking system, an acoustic tracking system, an accelerometer tracking system. Nevertheless, the tracking system can include any appropriate portions, such as an appropriate localizer for the tracking system and appropriate tracking devices for the tracking system. Thus, the discussion herein regarding an electromagnetic tracking system is merely exemplary of any appropriate tracking system. Also, more than one tracking system can be used during a procedure, such as a hybrid system discussed above. Thus, an EM and an optical tracking system can be used at the same time to track a tracking device within the same space.

Briefly, the navigation system 20 operates as follows. The navigation system 20 creates a translation map between all points in the image data or image space and the corresponding points in the patient's anatomy in patient space. After this map is established, the image space and patient space are registered. In other words, registration is the process of determining how to correlate a position in image space with a corresponding point in real or patient space. This can also be used to illustrate a position of the instrument 24 relative to the proposed trajectory and/or the determined anatomical target. The work station 42 in combination with the coil array controller 54 and the C-arm controller 34 identify the corresponding point on the pre-acquired image or atlas model relative to the tracked instrument 24 and display the position on display device 22 and relative to the image data 23. This identification is known as navigation or localization. An icon representing the localized point or instruments is shown on the display device 22 within several two-dimensional image planes, as well as on three and four dimensional images and models.

To register the patient 28, the surgeon 21 may use point registration by selecting and storing particular points from the pre-acquired images and then touching the corresponding points on the patient's 28 anatomy with a pointer probe or any appropriate tracked device, such as the instrument 24. The navigation system 20 analyzes the relationship between the two sets of points that are selected and computes a match, which allows for a determination of a correlation of every point in the image data or image space with its corresponding point on the patient's anatomy or the patient space.

The points that are selected to perform registration or form a translation map are the fiducial markers 69, such as anatomical or artificial landmarks. Again, the fiducial markers 69 are identifiable on the images and identifiable and accessible on the patient 28. The fiducial markers 69 can be artificial landmarks that are positioned on the patient 28 or anatomical landmarks that can be easily identified in the image data. The artificial fiducial markers 69, can also form part of the dynamic reference frame 58, such as those disclosed in U.S. Pat. No. 6,381,485, entitled "Registration of Human Anatomy Integrated for Electromagnetic Localization," issued Apr. 30, 2002, herein incorporated by reference. It will be understood that the "X" illustrated in FIG. 1 can merely indicate a position of a fiducial marker 69 rather than being the fiducial marker 69.

The system 20 may also perform registration using anatomic surface information or path information as is known in the art (and may be referred to as auto-registration). The system 20 may also perform 2D to 3D registration by utilizing the acquired 2D images to register 3D volume images by use of contour algorithms, point algorithms or density comparison algorithms, as is known in the art. An exemplary 2D to 3D registration procedure is set forth in U.S. Ser. No. 10/644,680, filed on Aug. 20, 2003, now U.S. Pat. App. Pub. No. 2004-0215071, entitled "Method and Apparatus for Performing 2D to 3D Registration", incorporated herein by reference.

In order to maintain registration accuracy, the navigation system 20 can continuously track the position of the patient 28 during registration and navigation with the dynamic reference frame 58. This is because the patient 28, dynamic reference frame 58, and transmitter coil array 52 may all move during the procedure, even when this movement is not desired. Alternatively, the patient 28 may be held immobile once the registration has occurred, such as with a head frame. Therefore, if the navigation system 20 did not track the position of the patient 28 or area of the anatomy, any patient movement after image acquisition would result in inaccurate navigation within that image. The dynamic reference frame 58 allows the tracking system 50 to track the anatomy and can assist in registration. Because the dynamic reference frame 58 is rigidly fixed to the patient 28, any movement of the anatomy or the transmitter coil array 52 is detected as the relative motion between the transmitter coil array 52 and the dynamic reference frame 58. This relative motion is communicated to the coil array controller 54, via the navigation probe interface 56, which updates the registration correlation to thereby maintain accurate navigation.

The dynamic reference frame 58 can be affixed to any appropriate portion of the patient 28, and can be used to register the patient space to the image data or image space, as discussed above. For example, when a procedure is being performed relative to a cranium 29, the dynamic reference frame 58 can be interconnected with the cranium 29. The dynamic reference frame 58 can be interconnected with the cranium 29 in any appropriate manner, such as those discussed herein according to various embodiments.

The navigation system 20 can detect both the position of the patient's anatomy and the position of the device 58 or attachment member (e.g. tracking device 31) attached to the instrument 24. Knowing the location of these two items allows the navigation system 20 to compute and display the position of the instrument 24 or any portion thereof in relation to the patient 28, after registration. The tracking system 50 is employed to track the instrument 24 and the anatomy 28 simultaneously, as discussed above according to various embodiments.

To obtain maximum accuracy it can be selected to fix the dynamic reference frame 58 in each of at least 6 degrees of freedom. Thus, the dynamic reference frame 58 or any of the tracking sensors 258 can be fixed relative to axial motion X, translational motion Y, rotational motion Z, yaw, pitch, and roll relative to the portion of the patient 28 to which it is attached. Any appropriate coordinate system can be used to describe the various degrees of freedom. Fixing the dynamic reference frame 58 relative to the patient 28 in this manner can assist in maintaining maximum accuracy of the navigation system 20.

The instrument 24 can be any appropriate instrument (e.g., a cannula, a catheter, a probe, a guide, a magnetic stimulator, etc.) and can be used for various procedures and methods, such as delivering a therapy, such as a material or stimulus, to a selected portion of the patient 28, such as within the cranium 29. Other exemplary instruments can also be implantable members, scissors, clamps, retractors, etc. The material can be any appropriate material such as a bioactive material, a pharmacological material, a contrast agent, or any appropriate material. The stimulus can include an electrical stimulus provided by a probe to the brain or spinal cord. As discussed further herein, the instrument 24 can be precisely positioned via the navigation system 20 and otherwise used to achieve a protocol for positioning the material relative to the patient 28 in any appropriate manner, such as within the cranium 29. The instrument 24 may also include a brain probe to perform deep brain stimulation.

The delivery of a material, performing an intervention or procedure, or providing a therapy to the anatomy can be assisted with images obtained by the imaging device 26. The imaging device 26 can obtain images of the patient 28 for display on the display device 22. Surgical navigation can assist the user in performing the procedure. An icon 100' (FIG. 7), illustrating a position of the instrument 24 relative to the patient 28, can be displayed on the display device 22 relative to the image data 23. This can assist the surgeon 21 in determining the position of the instrument 24 relative to the patient 28 and relative to a planned position of the instrument 24.

As discussed above, the instrument 24 can include the TMS probe 100. The TMS probe 100 can include appropriate portions, such as a handle or graspable portion 104 and the coil portions 102. It will be understood that the coil portion 102 can be provided as two coils 102a, 102b in a substantially figure "8" configuration or any other appropriate configuration. The TMS probe 100 can be provided as any appropriate system, such as the MAGPRO X100™ TMS probe system provided by Medtronic, Inc. of the USA. One skilled in the art will understand the operation of the TMS probe 100, and the discussion herein is merely exemplary. Further, the TMS probe 100 can be provided in multiple configurations including a single coil, two coplanar coils, two coils provided at an angle relative to one another, or combinations thereof.

Further, the coils can include selected centers 106a, 106b. The centers 106a, 106b can be provided of any appropriate size to create a selected field relative to the TMS probe 100. As one skilled in the art will understand, the size of the coils, the size of the center openings 106a, 106b, and other appropriate dimensions, power provisions, and the like can be used to create a selected stimulation or magnetic field.

Generally, a current can be driven through the coil 102 which will produce a magnetic field substantially perpendicular to the direction of the current. For example, a magnetic field can be produced in the direction of arrows 108a and 108b. The magnetic fields, generally in the direction of arrows 108a, 108b, can cooperate to produce a sharper or larger spike along an axis of where the two coils 102a, 102b meet. For example, a combined or cooperative field can move in the direction of arrow 110 and be provided between the two coils 102a, 102b. The cooperative field position/direction, generally illustrated by arrow 110, can be substantially focused, minimally dispersed, and strong relative to the two individual fields produced by the two coils 102a, 102b. Therefore, the area of stimulation, which is the area being affected by the cooperative field of the TMS probe 100, can be substantially precise and strong. For example, the TMS probe 100 can form a focused stimulation region 112 that is a distance 112a from the center of the first coil 102a and 112b from the center of the second coil 102b.

The determination of the focused region 112 can be determined in any appropriate manner. For example, the TMS probe 100 can be calibrated using a generally known calibration system and technique to determine the focused region 112. The position of the focused region 112 can be stored in the memory system 46 for access during navigation of the probe 100.

The memory system 46 can be used to store the focused region 112 substantially intraoperatively, preoperatively, or at any appropriate time. Further, multiple localized regions can be determined or stored for a plurality of TMS probes, such as TMS probes of different configurations, manufacture, and the like. Therefore, once the TMS probe 100 is used on a patient 28, the position of the focused region 112, relative to a point on the TMS probe 100, can be determined. Generally, the centers of the coils 102a, 102b are fixed relative to various regions of the TMS probe 100. Therefore, the position of the focused region 112 can also be known relative to any appropriate position or location on the TMS probe 100.

Because the position of the focused region 112 is known relative to various portions of the TMS probe 100, the focused region 112 can be tracked or navigated relative to the patient 28. The navigation of the focused region 112 can be based upon a tracked or determined location of the TMS probe 100, according to various embodiments. The TMS probe 100 can be tracked with the tracking system 50 to determine a location of the TMS probe 100 relative to the patient 28.

A determination of position of the TMS probe 100 relative to the patient 28 can then be used to determine the position of the focused region 112 relative to the patient 28. Further, planned positions for a focused stimulation, such as a planned position 160 (FIG. 7) of the focused region 112 relative to the patient 28, can also be determined and the TMS probe 100 can be navigated or moved to the appropriate location to achieve the planned positioning and stimulation. The planned position 160 can be any appropriate position determined pre-operatively or intra-operatively. The panned position or stimulation region 160 can also be displayed on the image data, as discussed herein.

With continuing reference to FIG. 2, the TMS probe 100 can include various portions that are a part of the tracking system 50. For example, the TMS probe 100 can include or be associated with the tracking device 31. The tracking device 31 can be tracked with the tracking system 50 to determine a location of the tracking device 31. As discussed above, image data can be displayed on the display 22, and illustrated further herein, along with an icon 100' illustrating the position of the TMS probe 100 relative to the patient 28.

Further, the alternative localizer 52b can be associated with the TMS probe 100. The localizer 52b can be affixed to the TMS probe in any appropriate manner, such as adhesives, injection molding of an appropriate body, or any other appropriate method. Nevertheless, the localizer 52b can be associated with the TMS probe 100 to allow for the creation of the localizing field from a position of the TMS probe 100. Positioning the localizer 52b on the TMS probe 100 can allow for positioning the localizer 52b and the field produced by it substantially near the area being navigated, within a single unit, and to various other advantages. Nevertheless, it will be understood that the localizer can be provided at any appropriate location, such as with the localizer 52 and 52*a*. The provision of the localizer 52*b* on the TMS probe 100, however, is merely exemplary and can provide a substantially mobile system.

With reference to FIGS. 1 and 2, the TMS probe 100 is generally operated with a TMS probe driver or stimulator system. The TMS probe system can be integrated with the processing system 40 in the work station 42. The signal can be transmitted along line 120 to the array controller 54 and line 21 to the TMS probe 100. It will be understood, however, that the control and stimulator portion for the TMS probe 100 can be provided as a separate system as opposed to being integrated with the work station 42. The separate system can allow the TMS probe 100 to be substantially independent and mobile relative to the navigation system 20. Nevertheless, the navigation system 20 can include the integrated TMS probe controller to provide a substantially single unit system. In addition, the controller portion of the TMS probe 100 can be connected to the workstation 42 for use during navigation and disconnected thereafter. Therefore, the user input 44 and the display 22 can be used to display the image data 23, the icon 100' representing a position of the TMS probe 100 or other appropriate instrument 24 relative to the patient 28, and the control features for the TMS probe 100. As is understood, the work station 42 can also be provided in a substantially mobile manner to allow for movement of the navigation system 20 to various locations for use by the user 21.

As discussed above, the TMS probe 100, according to various embodiments, operates by producing or inducing an electric stimulation within a conductive material. The induction is formed by moving a current through the coils 102*a*, 102*b* of the TMS probe 100. According to various embodiments, the localizers 52, 52, 52*b* also produce magnetic or electromagnetic fields by moving a current through a coil or multiple coils defining the localizers 52, 52*a*, 52*b*. The two currents can be provided at different frequencies. For example, the localizer frequency can be about two kilohertz (kHz) while the frequency for the TMS probe 100 can be about four kHz. If the frequencies are different the localizer arrays 52-52*b* and the TMS probe 100 can be operated substantially simultaneously and the processor system 40 or the navigation system 50 can be used to remove the interference of the multiple frequencies to track the tracking devices 31 and 62. Thus, the TMS probe 100 and the tracking system 50 can be operated substantially simultaneously according to various embodiments. Alternatively, the TMS probe can be operated separately or at a distinct time period from the tracking system 50. For example, the TMS probe 100 can be tracked relative to the patient 28 using the tracking system and then the TMS probe 100 can be energized to stimulate a selected portion of the anatomy. It will be understood that various other components can be provided, such as a robotic arm, a mechanical linkage 150, or the like to hold the TMS probe 100 in a selected location. Therefore, according to various embodiments, the TMS probe 100 can be navigated relative to the patient 28 and the linkage system 150 (FIG. 1) can be interconnected with the TMS probe 100 to hold the TMS probe 100 relative to the patient 28 in a selected position.

Figures 3, 4:
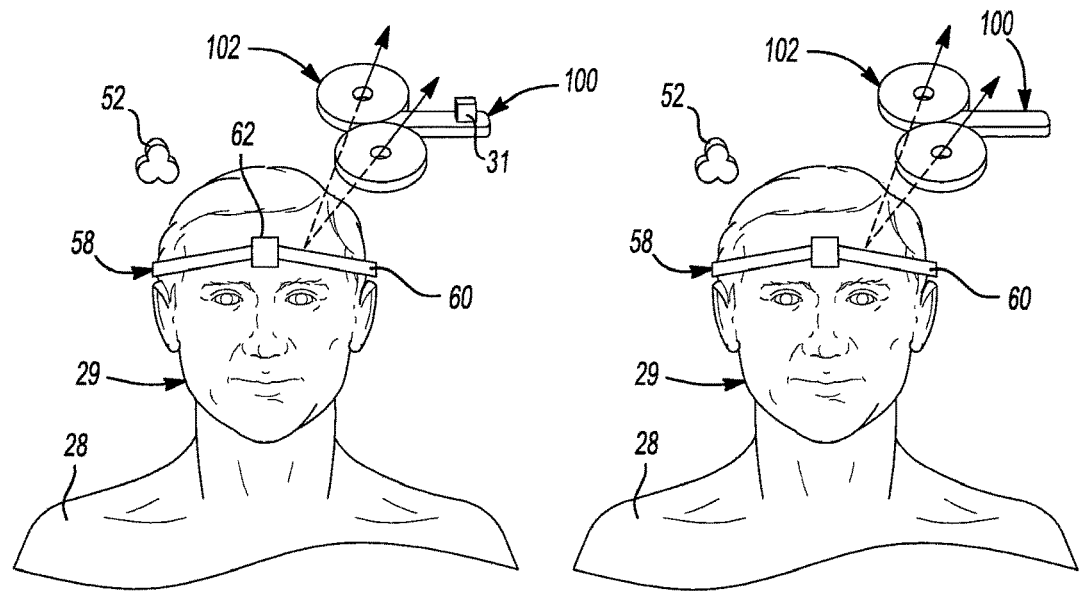
FIG. 3 is an environmental view of a magnetic stimulation device navigation system according to various embodiments.
FIG. 4 is an environmental view of a magnetic stimulation device navigation system according to various embodiments.

With reference to FIG. 3, according to various embodiments, the TMS probe 100 can be associated with the tracking device 31. The tracking device 31 can be associated with the TMS probe in any appropriate manner. For example, the tracking device 31 can be adhered to a graspable portion of the TMS probe 100. Alternatively, the tracking device 31 can include a housing that is molded with the TMS probe 100 to house the coils for the tracking device 31. Further, as discussed above, the tracking device 31 can include one or multiple coils that are provided to either sense an electromagnetic field or transmit an electromagnetic field.

The TMS probe 100 can be moved relative to the patient 28 in any appropriate manner, such as by the surgeon 21 or with a holding device, such as the stand 150. Regardless, the TMS probe 100 can be moved relative to the patient 28. The tracking device 31 can be used in the tracking system 50 to determine the position of the tracking device 31 and the probe 100 in a coordinate system.

Associated with the patient 28, such as connected to the cranium 29, can be the dynamic reference frame tracking device 62. The dynamic reference frame 58, which can include the base 60 attached to the cranium 29, can be used by the tracking system 50 to determine a position of the cranium 29. As discussed above, the dynamic reference frame 58 can be interconnected with the cranium 29 of the patient 28 to determine a position of the cranium 29 in the patient space. The position of the dynamic reference frame 58 can be localized or registered to the image data 23 so that the display of the image data 23 can be displayed based upon the location or movement of the cranium 29. The dynamic reference frame 58 can be provided to determine movement of the cranium 29, either inadvertent or planned movement. The determination of the position of the dynamic reference frame 58 can also be used to determine a relative position of the TMS probe 100 relative to the cranium 29.

The localizer array 52 can produce a field that is sensed by both the dynamic reference frame 58 and the tracking device 31. Although, as discussed above, the opposite may be true, where the tracking devices 31, 62 transmit a field and the localizer array 52 senses the field. The discussion of the localizer array 52, herein and above, is merely exemplary and one skilled in the art will understand that the use of the localizer array 52 as a transmitting device will be provided for clarity and brevity of the current discussion.

The determination of the position of the tracking device 62 associated with the dynamic reference frame and the tracking device 31 associated with the TMS probe 100 can be used to determine relative positions of the cranium 29 and the TMS probe 100. Therefore, appropriate representations can be provided on the display 22 of the image data of the cranium 29 and an icon, such as the icon 100', representing the TMS probe 100. The determination of the relative positions can be made by the processor system 40.

In other words the localizer system 52, can produce a field, according to various embodiments, that is sensed by the tracking devices 31, 62. The sensing can include an induced voltage. The induced voltage can produce a signal that is sent to the tracking system NPI 56. The tracking system 50, then, can determine the position of the tracking devices 31, 62 in the field. This can be used, therefore, to determine the relative positions of the TMS probe 100 and the patient 28. In addition, if the patient space and image space are registered, the navigation processor 40 can also determine the position of the TMS probe 100 in image space and display an appropriate icon on the display device 22, as discussed below.

Figure 7:
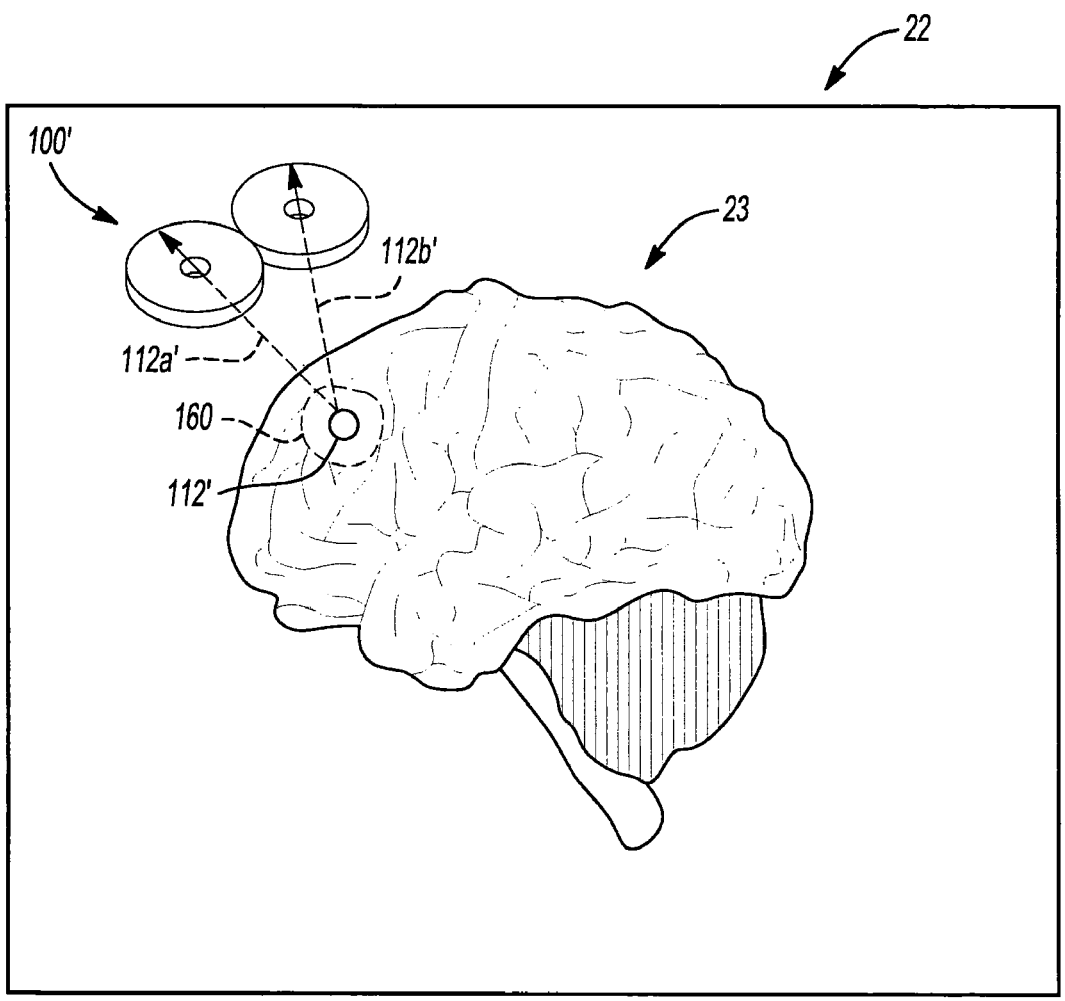
FIG. 7 is a plan view of a display device displaying image data and an icon representing a position of an instrument relative to the image data.

Briefly turning reference to FIG. 7, the display device 22 can display the image data 23. Further, the display device 22 can display the icon 100' illustrating the relative position of the TMS probe 100 to the patient 28, for example the brain of the patient 28. Further, various other icons can be provided on the display device, such as an icon 112' illustrating the substantially focused area 112 produced by the TMS probe 100. Various lines or vectors 112*a*' and 112*b*' can be illustrated to show the general area of the field being produced by the TMS probe 100. Therefore, the display device 22 can illustrate both the position of the TMS probe 100 and the focused area 112. The icons on the display 22 can be used by a user, such as the surgeon 21, to determine whether the TMS probe is stimulating a selected area of the anatomy.

For example, the planned region 160 can be illustrated on the display device 22. The planned region 160 can be any appropriate region, such as an optical center, an auditory center, a verbal center, or the like in the brain or the patient 28. Nevertheless, the planned area 160 can be substantially the area which is planned to receive the stimulation to be provided by the TMS probe 100. The various icons and the display can assist the user in moving the TMS probe 100 until the focused area icon 112' is within the planned region 160. Further, the display device 22 can be controlled to provide a visual feedback that the focused area 112 is within the planned area 160. For example, the planned area 160 can change colors, flash, or include other appropriate visual signals to indicate to the user 21 that the focused region 112 is within the planned area 160.

A plan can be produced at any appropriate time, such as substantially preoperatively. The plan can be stored in the memory system 46 and can be based upon pre-acquired image data, atlas model image data, or any other appropriate data. Further, the plan can be based upon an appropriate or selected stimulation of the brain of the patient 28. The plan can be a specialized plan produced by the user 21, a standardized plan, or any other appropriate plan. Nevertheless, the display device 22 can display the planned area 160 for viewing by the user 21 to assist in determining an appropriate navigated location of the TMS probe 100 relative to the patient 28. Further, the processing system 40 can process the image data 23 and display the icons 100', 112', 112*a*', 112*b*', and 160 for viewing by the user 21. The processor system 40 can further determine the navigation to determine the location of the TMS probe 100 relative to the patient 28. The determined location can be displayed with the appropriate icons and the image data 23.

With additional reference to FIG. 3, the tracking system 50 can use the relative positions of the dynamic reference frame 58 and the tracking device 31 on the TMS probe 100 to allow the processor system 40 to display the icons on the display device 22 at the appropriate locations. The tracking device 31 on the TMS probe 100 can be used by the navigation system 20 to determine the location of the TMS probe 100 relative to the patient 28. An appropriate therapy can then be applied to the patient, such as an appropriate number of pulses, a duration of pulses, or the like.

With reference to FIG. 4, and FIG. 7, the position of the TMS probe 100 can be determined according to various embodiments. For example, as discussed above, the TMS probe 100 includes one or more coils 102 that are operable to produce an electromagnetic field that can induce a current in a conductive material, which can stimulate the brain of the patient 28. As an alternative, or in addition to the tracking device 31, illustrated in FIG. 3, the coils 102 can also act as the tracking device that can be tracked with the tracking system 50.

The localizer 52 can emit a field that induces a voltage in the coils 102 the TMS probe 100, in a manner that is similar to the inducement of a voltage in the tracking device 31. The voltage can produce a signal that is transmitted to the NPI 56. A determination of the position of the coils 102 within the field, produced by the localizer array 52, can then be determined. The dynamic reference frame 58 can be attached to the cranium 29 of the patient 28. The position of the dynamic reference frame 58 relative to the TMS probe 100 can also be determined.

The elimination of the tracking device 31, according to various embodiments, can be used when a voltage is induced in the coils 102 of the TMS probe 100. As discussed above, the field emitted by the localizer device 52 can be at a different frequency than the stimulation frequency of the TMS probe 100. Therefore, the systems can be provided to operate substantially in a non-interfering manner.

In addition, the coils 102 of the TMS probe 100 can be augmented to include a separate coil that can be used as a tracking device. For example, the coils 102 of the TMS probe 100 can be wrapped around the centers 106*a*, 106*b*, as illustrated in FIG. 2. A separate winding can be provided either coaxial with the coils 102 of the TMS probe 100 or substantially perpendicular to the coils 102 of the TMS probe 100. It will be understood that windings can be provided in any appropriate orientation relative to the coils 102, coaxial and perpendicular are merely exemplary.

Nevertheless, the provision of the coils 102 of the TMS probe 100 or a coil provided substantially integrally therewith can be used as a tracking portion that is alternative to the tracking device 31. The coil 102 can be used to provide the same information to the tracking system 50 as the tracking device 31. Thus, the position of the TMS probe 100 can be determined relative to the patient 28, such as relative to the DRF 58.

In other words, the coil 102 of the TMS probe 100 can be used as the tracking device that reacts to the field produced by the localizer system 52, according to various embodiments. The tracking system can determine the position of the coil 102 in the field produced by the localizer system 52. The position of various portions relative to the coils 102 can be determined, for example the location of the focused region 112. In addition, the position of the DRF 58 can be determined. Thus, the relative positions of the TMS probe 100 and the patient 28 can be determined.

Briefly, the determination of the TMS probe 100 relative to the dynamic reference frame 58 can allow the processor system 40 to illustrate on the display device 22 the relative position of the TMS probe 100 to the image data 23 of the patient 28. As discussed above, the image space and the patient space can be registered according to various embodiments. As illustrated in FIG. 7, icons can be displayed on the display device 22 to illustrate both the positions of the TMS probe 100 and the position of the anatomy of interest, such as the brain.

Figures 5, 6:
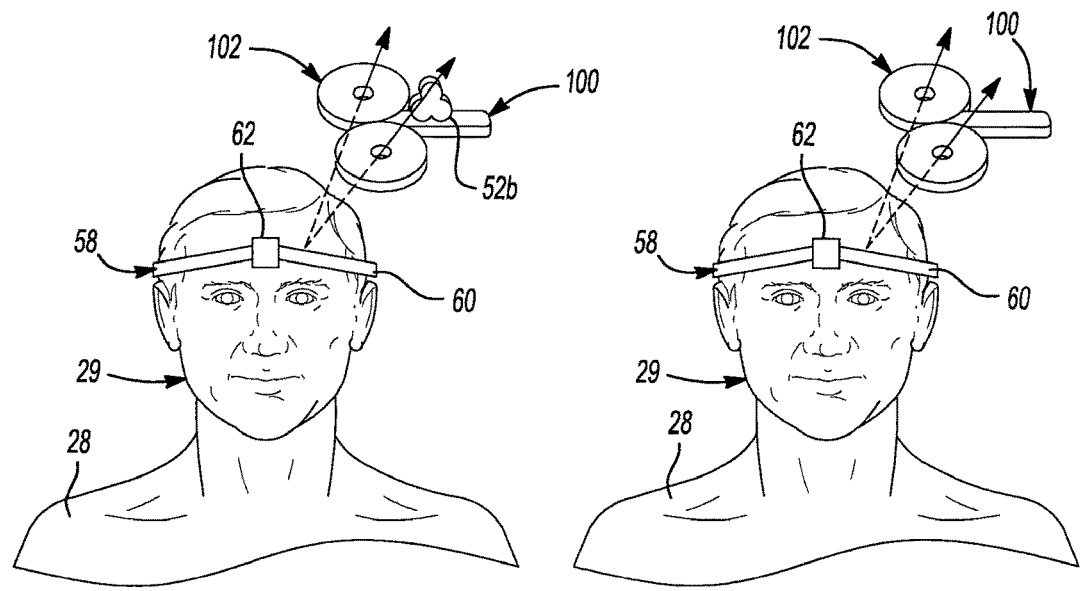
FIG. 5 is an environmental view of a magnetic stimulation device navigation system according to various embodiments.
FIG. 6 is an environmental view of a magnetic stimulation device navigation system according to various embodiments.

With reference to FIGS. 5 and 7, the localizer device 52*b* can be provided on the TMS probe 100, according to various embodiments. For example, the localizer device 52*b* can be adhered to the TMS probe 100 using various adhesives or connecting devices. Alternatively, or in addition thereto, the TMS probe 100 can include a molded portion to enclose the various portions of the localizer device 52*b*, such as the coil array. The body of the TMS probe 100 and the housing for the localizer array 52*b* can be injection molded or molded according to any appropriate technique of an appropriate material.

The integration of the localizer device 52*b* and the TMS probe 100 can allow the field produced by the localizer array 52*b* to be substantially near the TMS probe 100. As discussed herein, the localizer array 52 can be the "origin" of the tracking system. Alternatively, the DRF 58 can be the origin and its position relative to the localizer array 52*b* is tracked. Regardless, the position of the TMS probe 100 can be known or determined relative to the origin of the field produced by the localizer system 52*b*. Alternatively, according to various embodiments, the position of the probe can be determined as the position of the localizer system 52*b* receiving or sensing fields produced by the tracking device 31.

The field produced by the localizer device 52*b* can be used to determine the location of the dynamic reference frame 58 within the field produced by the localizer device 52*b*. The position of the dynamic reference frame 58 within the field produced by the localizer device 52*b* can be used to determine the position of the dynamic reference frame 58 relative to the localizer device 52*b*. The position of the TMS probe 100 relative to the DRF 58 can be determined because the localizer 52*b* is interconnected with the TMS probe 100. In other words, the position of the TMS probe 100 relative to the localizer device 52*b* can then be used to determine the position of the TMS probe 100 relative to the dynamic reference frame 58.

The relative positions of the TMS probe 100 and the dynamic reference frame 58 can then be used to determine the position of the TMS probe 100 relative to the patient 28, and the cranium 29 of the patient 28. The position of the TMS probe 100 is known based upon its fixed relative position to the localizer device 52*b*. The position of the DRF 58 in the field of the localizer 52*b* is determined. Thus, the position of the TMS probe 100 relative to the DRF 52 can be determined.

The memory system 46 can include a stored position, such as a relative position of the localizer device 52*b* relative to the TMS probe 100. Therefore, the determined position of the dynamic reference frame 58 to the localizer device 52*b* can be used to determine the position of the TMS probe 100 relative to the dynamic reference frame 58. That determination can then be used to determine the position of the TMS probe relative to any position of the anatomy of the patient 28. Processor system 40 can make the various determinations and also display on the display device 22 the determined positions of the TMS probe 100 and the anatomy.

As illustrated in FIG. 7, the icons representing the TMS probe 100 and the image data can be displayed on the display device 22. The determined relative positions of the various portions in patient space can also be displayed on the display device 22.

With reference to FIGS. 6 and 7, a determination of the position of the TMS probe 100 relative to the patient 28 can be based upon or can use the field produced by the TMS probe 100. As discussed above, the TMS probe 100 includes one or more coils 102 that are operable to produce or emit an electromagnetic field. The electromagnetic field produced by the TMS probe 100 can be used to produce or induce a voltage within the tracking device 62 of the dynamic reference frame 58. The field produced by the TMS probe 100 can be provided at an appropriate frequency, according to various embodiments, to induce a signal within the tracking device 62 of the dynamic reference frame 58. The position of the dynamic reference frame 58 within the field, produced by the TMS probe 100 can then be determined, such as with the processor system 40. The determination of the position of the dynamic reference frame 58 within the field produced by the TMS probe 100 can be used to determine the position of the TMS probe 100 relative to the patient 28.

As discussed above, the dynamic reference frame 58 can be localized on the patient 28 relative to the image data 23. Therefore, determining the position of the dynamic reference frame 58 within the field produced by the TMS probe 100 can be used to determine the relative position of the TMS probe 100 to the patient 28. In other words, the origin of the localization field will be the TMS probe 100 or the coils 102. Thus, the determined or sensed field of the DRF 58 will be relative to the origin of the field produced by the TMS probe 100. This information can allow the processor system 40 to determine the relative positions of the DRF 58 and the TMS probe 100. The illustration of the relative position of the TMS probe and the anatomy of the patient, such as the brain, can be displayed on the display device 22, as illustrated in FIG. 7.

The TMS probe 100 can be provided to create a field that can be sensed by the dynamic reference frame 58. It will be understood, that the dynamic reference frame, in particular, the tracking device 62 of the dynamic reference frame 58, can be positioned substantially near the area to be stimulated or where the TMS probe 100 will be positioned to stimulate the planned area in the anatomy. Therefore, the tracking device 62 of the dynamic reference frame 58 can be positioned within the field produced by the TMS probe 100. Further, as discussed above, the TMS probe 100 can be fixed in a selected location with the holding device 150. Therefore, the TMS probe 100 can be navigated relative to a selected portion of the anatomy of the patient 28 and can be fixed there with the holding device 150.

According to various embodiments, such as those illustrated above, the TMS probe 100 can be navigated to a selected portion of the anatomy of the patient 28. The navigation of the TMS probe 100 relative to the appropriate portion of the patient 28 can be based upon any appropriate method. Nevertheless, the positioning of the TMS probe 100 relative to the patient 28 can be used to stimulate a selected portion of the anatomy according to a selected manner.

Figure 8:
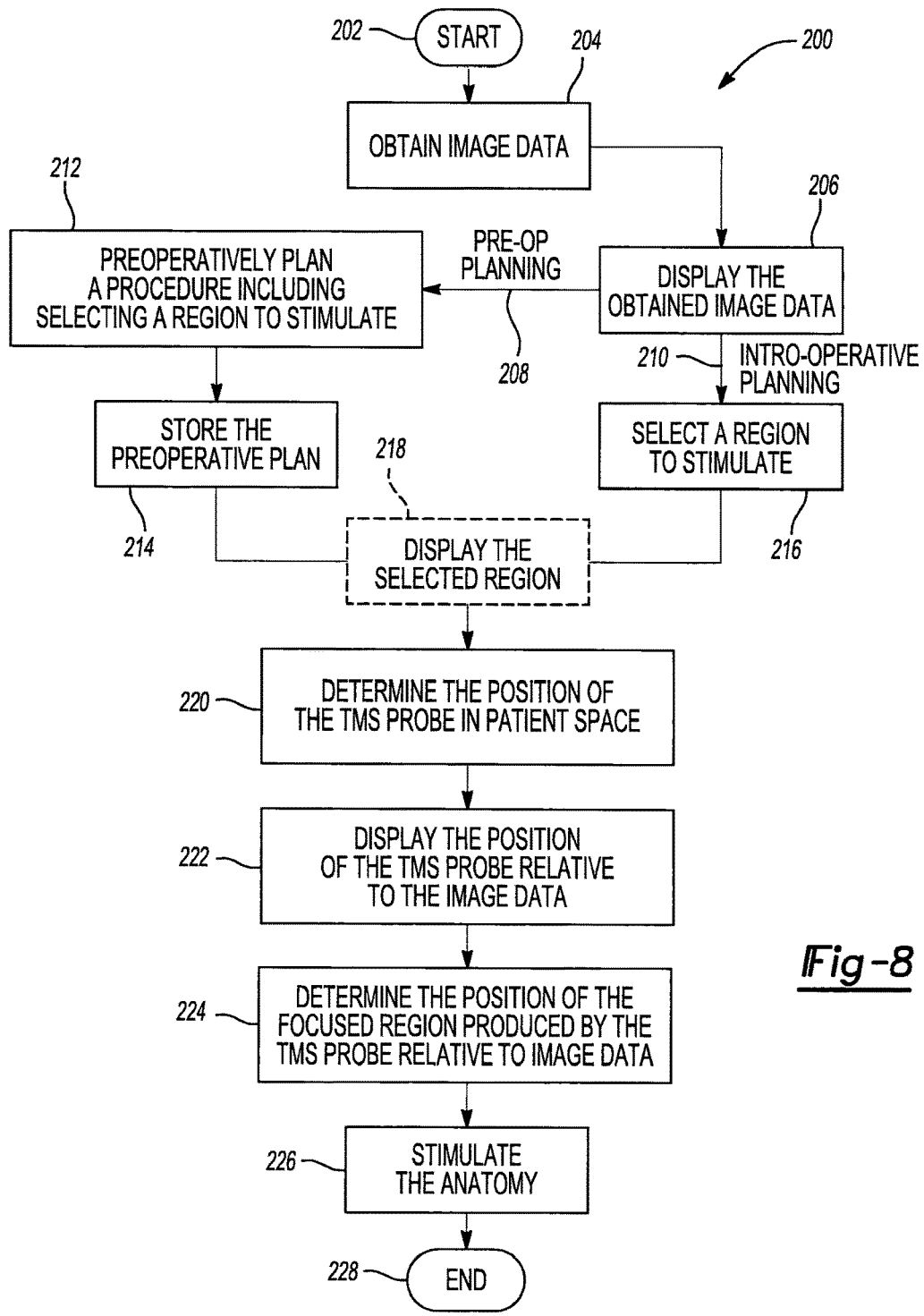
FIG. 8 is a flow chart of a method of navigating an instrument.

With reference to FIG. 8, an illustration of a method 200 of tracking a navigated magnetic stimulation instrument, such as the TMS probe 100 is illustrated. The method 200 of navigating the TMS probe 100 can begin in start block 202. Next, or at any appropriate time, image data of the patient 28 can be obtained in block 204.

The image data obtained of the patient 28 can be any appropriate image data. For example, the image data can include two dimensional or three dimensional image data. Further, the modality for obtaining the image data can be any appropriate type. For example, the image data can include magnetic resonance image data, computer tomography image data, positron emission data, tomography or any appropriate image data. The image data can either be obtained preoperatively and stored in an appropriate memory system, such as the memory 46, or obtained intraoperatively during the stimulation procedure. Nevertheless, the image data can be obtained of the patient and can be used for the navigation procedure.

The image data can also be provided to be viewed on the display device 22. After the image data is obtained, the image data can be displayed, such as on the display device 22, in block 206. The display of the image data in block 206 can be performed for various reasons.

At least two paths can be followed when performing the stimulation procedure. One path can be a preoperative plan path 208. Alternatively, or in addition thereto, an intraoperative plan can be produced when following path 210. The diverging paths of preoperative planning 208 and intraoperative planning 210 can also converge and be used simultaneously, as discussed further herein.

If the preoperative planning path is followed in path 208, then preoperative planning of a procedure, including selecting a region to stimulate, can be performed in block 212. The preoperative planning can include various portions, such as an amount of stimulation, a length of stimulation, a position of stimulation, and the like. For example, selecting a region to stimulate can be based upon selecting an affected area of the brain, an affected area of the anatomy, an area to be studied, or the like. For example, it may be selected to map a region of the brain of the patient 28 that affects speech. Therefore, selecting a region in the brain can be selecting a region that is generally associated with speech.

Once the preoperative plan has been created, the image data can be annotated with the preoperative plan. For example, the image data can be annotated with the selected region to be stimulated. As illustrated in FIG. 7, the area to be stimulated 160 can be illustrated with an icon. Therefore, as a part of the preoperative plan in block 212, the creation of the icon representing the area to be stimulated 160 can be created.

The preoperative plan can then be stored in block 214. The storing of the preoperative planning can include storing the region to be stimulated, storing the image data annotated with the region to be stimulated, storing the image data, and other appropriate information. The preoperative planning can be stored in the memory system 46 or in any appropriate accessible memory storage system.

If the preoperative plan path is not followed, the intraoperative planning path 210 can be followed. The intraoperative planning path 210 can proceed to selecting a region to stimulate in block 216. The region selected to be stimulated in block 216 can be any appropriate region. Further, the region to be stimulated can be substantially randomly chosen during a stimulation procedure based upon interaction of the patient with the user 21, the user's knowledge 21, or other appropriate indices. Further, the intraoperative selection of a region to stimulate in block 216 can be used for various research purposes. For example, a region of the brain can be randomly selected and stimulated and a determination of an effect on the anatomy can be studied. For example, a region of the brain can be stimulated and an evaluation of the patient's 28 speech patterns can be performed. Therefore, selecting a region intraoperatively in block 216 to be stimulated can be used to determine various portions of the brain that control various activities of the anatomy of the patient 28.

Regardless of the path followed, whether the preoperative planning 208 or the intraoperative planning path 210, the selected region to be stimulated can be displayed on the display device 22, optionally, in block 218. It will be understood that displaying a region to be stimulated need not be required. For example, the region to be stimulated can be stored in the memory system 26 and a robotic system can move the TMS probe 100 to an appropriate location relative to the patient 28 based upon the selected region to be stimulated. Therefore, displaying the selected region on the display device 22 is not required. Further, displaying a selected region to be stimulated can include displaying an icon representing a specific region to be stimulated on the display device 22. As discussed above, the determination of such a specific area of the anatomy, such as within the brain, need not be required.

During a procedure, the determination of the position of the TMS probe in patient space can be determined in block 220. The determination of the position of the TMS probe 100 can be based upon the tracking system 50 tracking the TMS probe 100, according to various embodiments including those discussed above. As discussed above, the position of the TMS probe 100 can be determined based upon various embodiments of the tracking system associated with the TMS probe 100. For example, the tracking device 31 can be associated with the TMS probe 100 to be tracked relative to the patient 28, such as relative to the dynamic reference frame 58. Nevertheless, various systems, according to various embodiments, can be used to track the position of the TMS probe and patient space. Generally, tracking the position of the TMS probe and patient space includes determining the position of the TMS probe relative to the patient.

Determining the position of the TMS probe 100 can allow displaying a position of the TMS probe in image space in block 222. Again, although it may be selected to display the position of the TMS probe in image space, such as with the icon 100', displaying the position of the TMS probe is not required. The position of the TMS probe can be used for various informative purposes for the user 21, but can also be optional information. For example, a robot or other control system can be used to move the TMS probe 100 to the patient 28.

In addition, the display of a position of the focused region can be produced on the image device 22 in block 224. The position of the focused region, or the region being stimulated, may be selected to be displayed on the display device 22 while not displaying the position of the probe 100 relative to the image data on the display device 22. The position of the TMS probe 100 relative to the patient 28 may not be as critical or as helpful as displaying the focused region 212 produced by the TMS probe 100. Therefore, the display of the position of the focused region 212 in block 224 can be displayed on the display device 22 without displaying other information.

As discussed above, the determination of the focused region of the TMS probe can be determined based upon its position relative to the portion being tracked, such as the tracking device 31. The position of the focused region can be determined in any appropriate manner, such as a calibration system, a factory determined position, or other appropriate determinations.

The anatomy can also be stimulated in block 226 such as generally where the focused region is produced. The anatomy can be stimulated in block 226 according to any appropriate manner, such as according to the preoperative plan in block 212 or according to any other appropriate indices, such as user experience. Then the procedure may end in block 228.

According to various embodiments, a probe, such as the TMS probe 100 can be tracked and navigated relative to the patient 28. The various embodiments can include multiple portions that work together or are associated with one another to allow tracking of the TMS probe 100. Alternatively, or in addition thereto, the TMS probe 100 can include various portions that can be used with an electromagnetic tracking system 50 to determine the position of the TMS probe 100 in patient space relative to the patient 28. As discussed above, the determination of the TMS probe 100 and patient space can then be used to determine the position of the TMS probe 100 and the focused region of the TMS probe 100 and image space. The determination of the position of the TMS probe 100 and the focused region 112, can be based upon a known position of the focused region 112 relative to the TMS probe and the registration of the image space and patient space, as discussed above. Therefore, a navigation system can be used to guide the TMS probe 100 relative to the selected region of the patient 28 to provide a stimulation thereto.

The teachings herein are merely exemplary in nature and, thus, variations that do not depart from the gist of the teachings are intended to be within the scope of the teachings. Such variations are not to be regarded as a departure from the spirit and scope of the teachings.

What is claimed is:

1. A system to navigate a procedure for a patient, comprising:
   a magnetic stimulation probe having a first conductive coil that is configured to operate in a first manner to produce a probe electromagnetic field having an electromagnetic focal region, the probe electromagnetic field being operable to induce a therapeutic current in a conductive material of the patient at the electromagnetic focal region; and
   an electromagnetic tracking system having an electromagnetic localizer configured to generate a localization field, the electromagnetic tracking system includes the first coil configured to operate in a second manner to sense the localization field or generate at least a portion of the localization field, wherein the electromagnetic tracking system further includes a processor configured to determine a position of the electromagnetic focal region relative to the patient based at least in part on the localization field produced by the electromagnetic localizer.

2. The system of claim 1, further comprising:
   a dynamic reference frame configured to be associated with the patient;
   wherein the electromagnetic localizer field is sensed by the dynamic reference frame.

3. The system of claim 2, wherein the first manner includes a first current at a first frequency that can be driven through the first conductive coil to produce the probe electromagnetic field; and
   the second manner includes a second current at a second frequency that can be driven through the first conductive coil to produce at least a portion of the localizer electromagnetic field.

4. The system of claim 3 wherein the first frequency is four kilohertz and the second frequency is two kilohertz.

5. The system of claim 1, wherein the magnetic stimulation probe further comprises a second conductive coil adjacent to the first conductive coil configured to operate in the first manner.

6. The system of claim 1, further comprising an imaging device to obtain image data of the patient, and a display device operable to display the image data of the patient, and an icon displaying a position of the focal region where the probe electromagnetic field is operable to induce the current in the conductive material.

7. The system of claim 6, wherein the display device is further operable to display a stimulation region icon that illustrates the selected position for stimulating the patient with the induced current.

8. The system of claim 1, further comprising:
   a memory system operable to store a procedure plan including a selected position for inducing a current in the patient.

9. A method to navigate a procedure for an anatomy of a patient, comprising:
   driving two coils of a magnetic stimulation probe to operate in a first manner to generate a focal region of an electromagnetic field, the focal region being a predetermined distance from the magnetic stimulation probe and being operable to induce a therapeutic current in a conductive material at a location in the anatomy of the patient at the focal region;
   tracking a position of the magnetic stimulation probe by operating at least one coil of the two coils in a second manner different than the first manner with an electromagnetic tracking system; and
   displaying image data of the patient and an icon representing the position of the focal region superimposed on displayed image data based upon a tracked position of the magnetic stimulation probe on a display device.

10. The method of claim 9, further comprising obtaining the image data of a portion of the patient.

11. The method of claim 10, wherein obtaining the image data of a portion of the patient includes obtaining at least one of magnetic resonance image data, tomography image data, positron emission tomography image data, and combinations thereof.

12. The method of claim 9, wherein tracking a position of the magnetic stimulation probe includes:
   operating the magnetic stimulation probe in the second manner to generate a localizing electromagnetic field and sensing the localizing electromagnetic field with a tracking device of a dynamic reference frame associated with the patient; and
   determining a relative position of the magnetic stimulation probe based on the dynamic reference frame.

13. The method of claim 9, wherein tracking a position of the magnetic stimulation probe includes:
   producing the localizing electromagnetic field with a localizer array separate from the magnetic stimulation probe; and
   determining a position of the two coils of the magnetic stimulation probe by sensing the localizing electromagnetic field with at least one coil of the two coils of the magnetic stimulation probe.

14. The method of claim 9, further comprising:
   determining a portion of the anatomy to be stimulated;
   navigating the focal region to the portion of the anatomy to be stimulated; and
   wherein displaying an icon representing the position of the focal region includes positioning the focal region in the determined area to be stimulated.

15. The method of claim 14, wherein determining the region of the anatomy to be stimulated occurs prior to the operation of the magnetic stimulation probe.

16. A system to navigate a procedure for a patient, comprising:
   an electromagnetic tracking system including an electromagnetic localizer system having at least a first conductive coil to be configured in a first manner to generate a localization field;
   a magnetic stimulation probe configured to be external to the patient and having second and third conductive coils, the second coil being configured to be switched to:
      i) operate as at least one of sense the localization field or operate as at least the first conductive coil of the electromagnetic localizer system to generate the localization field, and
      ii) produce a probe electromagnetic field when operated in a second manner different than the first manner, wherein the probe electromagnetic field is configured to induce a therapeutic current in a conductive material of the patient at a focal region; and
   a processor configured to determine a position of the focal region relative to the patient based at least in part on a localization field produced by the electromagnetic localizer system.

17. The system of claim 16, further comprising:
   a display device configured to display image data of the patient on the display device, the display device is further configured to display a position of the focal region based on a tracked position of the magnetic stimulation probe including a focal region icon representing the position of the focal region superimposed on the displayed image data based upon the tracked position of the magnetic stimulation probe due to at least sensing or generating a localizing electromagnetic field without displaying the location of the probe.

18. The system of claim 16, wherein the magnetic stimulation probe and the localizer are integrated as one instrument.

19. The system of claim 16, wherein the electromagnetic tracking system further includes a localizer array separate from the magnetic stimulation probe, wherein the localizer array is configured to produce the localization field a distance from the magnetic stimulation probe.

20. The system of claim 16, wherein the second and third coils are co-planar.

* * * * *